United States Patent [19]

Kikumoto et al.

[11] 4,220,603

[45] Sep. 2, 1980

[54] PHARMACEUTICALLY ACTIVE (OMEGA-AMINOALKOXY)BIBENZYLS

[75] Inventors: Ryoji Kikumoto, Machida; Kunihiro Ninomiya; Harukazu Fukami, both of Yokohama; Hiroto Hara, Machida, all of Japan

[73] Assignee: Mitsubishi Chemical Industries, Limited, Tokyo, Japan

[21] Appl. No.: 943,621

[22] Filed: Sep. 19, 1978

[30] Foreign Application Priority Data

Oct. 7, 1977 [JP] Japan .................................. 52/120710
Jul. 14, 1978 [JP] Japan .................................. 53/85833
Aug. 1, 1978 [JP] Japan .................................. 53/94044

[51] Int. Cl.$^2$ ............................................. C07C 93/06
[52] U.S. Cl. .................................. 260/570.7; 424/330
[58] Field of Search ................. 544/401; 424/250, 330; 260/570.7

[56] References Cited

U.S. PATENT DOCUMENTS

| | | | |
|---|---|---|---|
| 3,164,607 | 1/1965 | Lednicer .............................. | 544/401 |
| 3,375,256 | 3/1968 | Bach et al. .......................... | 544/401 |
| 3,476,767 | 11/1969 | Bencze ................................ | 544/401 |
| 4,024,282 | 5/1977 | Kikumoto et al. ................ | 260/570.7 |
| 4,071,559 | 1/1978 | Kikumoto et al. ................ | 260/570.7 |

*Primary Examiner*—Jose Tovar
*Attorney, Agent, or Firm*—Oblon, Fisher, Spivak, McClelland & Maier

[57] ABSTRACT

(Omega-aminoalkoxy)bibenzyls are prepared and found useful as pharmaceutical agents, particularly as inhibitors of platelet aggregation.

4 Claims, No Drawings

PHARMACEUTICALLY ACTIVE (OMEGA-AMINOALKOXY)BIBENZYLS

BACKGROUND OF THE INVENTION

Field of the Invention

This invention relates to (omega-aminoalkoxy)bibenzyls which are pharmacologically active as inhibitors of platelet aggregation. More particularly, this invention relates to 2-(omega-aminoalkoxy)bibenzyls and to pharmaceutical compositions containing the same effective for inhibiting platelet aggregation.

This invention also relates to processes whereby said (omegaaminoalkoxy)bibenzyls are prepared and also to processes for inhibiting platelet aggregation.

SUMMARY OF THE INVENTION

In summary, the compounds of this invention can be represented by the formula (I):

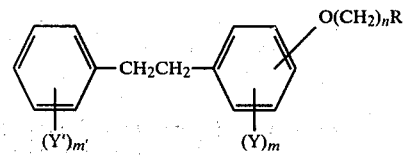

wherein R is (1)

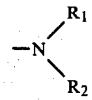

wherein $R_1$ and $R_2$ which are alike or different are selected from the group consisting of hydrogen, $C_1-C_8$ alkyl and $C_1-C_8$ hydroxyalkyl or (2)

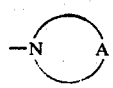

wherein A is a divalent radical which consists of two or more groups selected from methylene —$CH_2$—, monosubstituted methylene

and disubstituted methylene

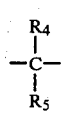

wherein $R_3$, $R_4$ and $R_5$ independently are $C_1-C_5$ alkyl, carboxyl, $C_2-C_6$ alkoxycarbonyl, hydroxyl or

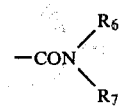

wherein $R_6$ and $R_7$ are hydrogen or $C_1-C_5$ alkyl; and zero or one or more than one group selected from the group consisting of oxy —O—, thio —S—, imino

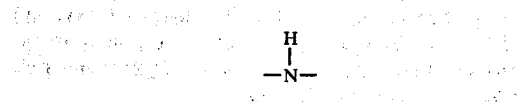

and substituted imino

wherein $R_8$ is $C_1-C_5$ alkyl or $C_1-C_5$ hydroxyalkyl, which are combined in an arbitrary order, the number of the combined groups being up to 9; each of the Y radicals and the Y' radicals is hydrogen, halogen, $C_1-C_5$ alkyl, hydroxyl, $C_1-C_5$ alkoxy, carboxyl, $C_2-C_6$ alkoxycarbonyl or

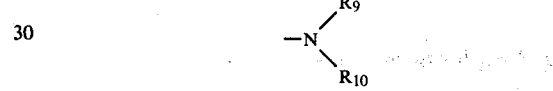

wherein $R_9$ and $R_{10}$ are hydrogen or $C_1-C_5$ alkyl; n is an integer of 2 to 8; m is an integer of 1 to 4; and m' is an integer of 1 to 5, or the acid addition salts thereof.

DESCRIPTION OF THE PREFERRED EMBODIMENTS

As summarized above, this invention relates to a group of compounds useful as pharmaceutical agents, the structure and numbering system of which are as follows:

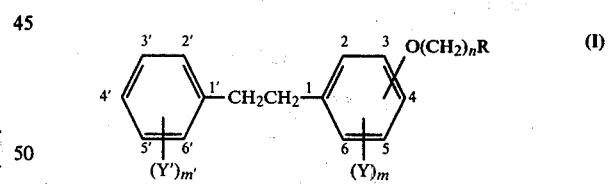

wherein R is represented by the formula (1)

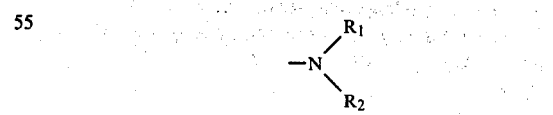

or (2)

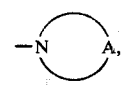

each of which will be described below in detail.

1. In case where R is

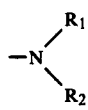

$R_1$ and $R_2$ which are alike or different are selected from the group consisting of hydrogen; alkyl of 1-8 (preferably 1-5) carbon atoms, such as methyl, ethyl, propyl, isopropyl, butyl, isobutyl, pentyl, hexyl, heptyl, octyl or the like; and hydroxyalkyl of 1-8 (preferably 1-5) carbon atoms, such as hydroxymethyl, 2-hydroxyethyl, 3-hydroxypropyl, 5-hydroxypentyl or the like.

2. In case where R is

A is a divalent radical which consists of two or more groups selected from methylene —$CH_2$—, monosubstituted methylene

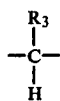

and disubstituted methylene

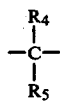

wherein $R_3$, $R_4$ and $R_5$ independently are alkyl of 1-5 (preferably 1-3) carbon atoms, such as methyl, ethyl, propyl, isopropyl, butyl or the like; carboxyl; alkoxycarbonyl of 2-6 (preferably 2-4) carbon atoms, such as methoxycarbonyl, ethoxycarbonyl, propoxycarbonyl, butoxycarbonyl or the like; hydroxyl; or

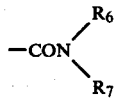

wherein $R_6$ and $R_7$ are hydrogen or alkyl of 1-5 (preferably 1-3) carbon atoms, such as carbamoyl, methylcarbamoyl, dimethylcarbamoyl, diethylcarbamoyl, propylcarbamoyl, butylcarbamoyl;

and zero or one or more than one group selected from the group consisting of oxy —O—, thio —S—, imino

and substituted imino

wherein $R_8$ is alkyl of 1-5 (preferably 1-3) carbon atoms, such as methyl, ethyl, propyl, butyl or the like; or hydroxyalkyl of 1-5 (preferably 1-3) carbon atoms, such as hydroxymethyl, 2-hydroxyethyl, 3-hydroxypropyl or the like, which are combined in an arbitrary order, the number of the combined groups being up to 9 (preferably 7).

Illustrative of the typical R groups are the following:

1. In case where R is

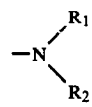

amino, methylamino, dimethylamino, ethylamino, diethylamino, propylamino, dipropylamino, isopropylamino, diisopropylamino, N-methyl-N-butylamino, dibutylamino, dipentylamino, dihexylamino, 2-hydroxyethylamino, bis (2-hydroxyethyl) amino, N-(2-hydroxyethyl)-N-methylamino.

2. In case where R is

1-aziridinyl, 1-azetidinyl, 1-pyrrolidinyl, piperidino, 1-hexamethyleneiminyl, 1-heptamethyleneiminyl, 1-piperazinyl, morpholino, thiazolidinyl, thiomorpholino, 3-methyl-1-pyrrolidinyl, 2,5-dimethyl-1-pyrrolidinyl, 2-ethylpyrrolidinyl, 2-methylpiperidino, 3-methylpiperidino, 4-methylpiperidino, 4-ethylpiperidino, 2,4-dimethylpiperidino, 4-methyl-1-piperazinyl, 4-ethyl-1-piperazinyl, 4-propyl-1-piperazinyl, 4-(2-hydroxyethyl)-1-piperazinyl, 4-(3-hydroxypropyl)-1-piperazinyl, 4-(2-hydroxyethyl)piperidino, carboxyaziridinyl, 3-carboxy-1-azetidinyl, 3-carboxy-1-pyrrolidinyl, 3-methoxycarbonyl-1-pyrrolidinyl, 2-carboxy-1-pyrrolidinyl, 3-dimethylcarbamoyl-1-pyrrolidinyl, 4-carboxypiperidino, 4-methoxycarbonylpiperidino, 4-dimethylcarbamoylpiperidino, 3-carboxypiperidino, 3-carbamoyl-1-pyrrolidinyl, 3-carbamoylpiperidino, 4-carboxy-1-hexamethyleneiminyl, 4-carbamoylpiperidino, 4-hydroxypiperidino, 3-hydroxypiperidino, 1-imidazolidinyl, 3-methyl-1-imidazolidinyl, 4-methylhexahydro-1,4-diazepinyl, 4-(2-hydroxyethyl)hexahydro-1,4-diazepinyl.

The preferred

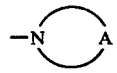

group can be represented by the formula (II):

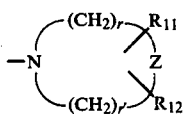

(II)

wherein Z is selected from the group consisting of —$CH_2$—, —O—, —NH—,

alkyl said alkyl containing 1 to 5 (preferably 1 to 3) carbon atoms and

hydroxyalkyl said hydroxyalkyl containing 1 to 5 (preferably 1 to 3) carbon atoms; $R_{11}$ and $R_{12}$ are selected from the group consisting of alkyl of 1–5 (preferably 1–3) carbon atoms, carboxyl, alkoxycarbonyl of 2–6 (preferably 2–4) carbon atoms, hydroxyl and

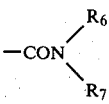

wherein $R_6$ and $R_7$ are hydrogen or alkyl of 1–5 (preferably 1–3) carbon atoms; and r and r' are each integers of 1, 2 or 3 (preferably, r+r' is 3 or 4).

The most preferred R groups are the following:
1. In case where R is

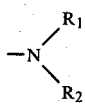

$C_1$–$C_5$ alkylamino, $C_2$–$C_6$ dialkylamino, $C_1$–$C_5$ ω-hydroxyalkylamino, $C_2$–$C_6$ N-(ω-hydroxyalkyl)-N-alkylamino and $C_2$–$C_6$ bis(ω-hydroxyalkyl) amino.
2. In case where R is

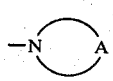

1-pyrrolidinyl, piperidino, morpholino, $C_6$–$C_8$ 4-alkyl-1-piperazinyl and $C_6$–$C_8$ 4-ω-hydroxyalkyl-1-piperazinyl, each of which is unsubstituted or substituted with one or two groups selected from carboxyl, $C_2$–$C_4$ alkoxycarbonyl, carbamoyl, $C_3$–$C_6$ N,N-dialkylcarbamoyl, $C_2$–$C_4$ N-alkylcarbamoyl, $C_1$–$C_3$ alkyl and hydroxyl.

In the above formula (I), each of the Y radicals and Y' radicals is hydrogen; halogen such as fluorine, chlorine and bromine; alkyl of 1–5 (preferably 1–3) carbon atoms, such as methyl, ethyl, propyl, butyl or the like; hydroxy; alkoxy of 1–5 (preferably 1–3) carbon atoms, such as methoxy, ethoxy, propoxy, butoxy or the like; carboxyl; alkoxycarbonyl of 2–6 (preferably 2–4) carbon atoms; such as methoxycarbonyl, ethoxycarbonyl or the like; amino; alkylamino of 1–5 (preferably 1–3) carbon atoms, such as methylamino, ethylamino, propylamino, butylamino or the like; or dialkylamino of 2–10 (preferably 2–6, and more preferably 2–4) carbon atoms, such as dimethylamino, diethylamino, dipropylamino or the like.

The preferred Y and Y' radicals are hydrogen, fluorine chlorine, $C_1$–$C_3$ alkyl, hydroxyl, $C_1$–$C_3$ alkoxy, carboxyl, $C_2$–$C_4$ alkoxycarbonyl and $C_2$–$C_4$ dialkylamino.

In the above formula (I), the omega-aminoalkoxy group may be located at any of the 2- to 4-position of the benzene nucleus; preferably, it is located at either the 2- or 4-position, and more preferably it is located at the 2-position.

In the above formula (I), n is an integer of 2 to 8, preferably 2 to 6, and more preferably 2 to 4; m is an integer of 1 to 4, preferably 1 or 2; and m' is an integer of 1 to 5, preferably 1 or 2.

Specific compounds in the scope of this nvention are:
2-(4-methylaminobutoxy)bibenzyl
2-(2-dimethylaminoethoxy)bibenzyl
2-(3-dimethylaminopropoxy)bibenzyl
2-(4-dimethylaminobutoxy)bibenzyl
2-(5-dimethylaminopentyloxy)bibenzyl
2-(6-dimethylaminohexyloxy)bibenzyl
2-(2-diethylaminoethoxy)bibenzyl
2-(3-diethylaminopropoxy)bibenzyl
2-(4-diethylaminobutoxy)bibenzyl
2-(5-diethylaminopentyloxy)bibenzyl
2-(6-diethylaminohexyloxy)bibenzyl
2-[4-(N-methyl-N-butylamino)butoxy]bibenzyl
2-{4-[N-methyl-N-(2-hydroxyethyl)amino]butoxy}-bibenzyl
2-[4-bis(2-hydroxyethyl)aminobutoxy]bibenzyl
4-(3-dimethylaminopropoxy)bibenzyl
4-(4-dimethylaminobutoxy)bibenzyl
2-[4-(1-pyrrolidinyl)butoxy]bibenzyl
2-(4-piperidinobutoxy)bibenzyl
2-(4-morpholinobutoxy)bibenzyl
2-[4-(4-hydroxypiperidino)butoxy]bibenzyl
2-[4-(1-piperazinyl)butoxy]bibenzyl
2-{4-[4-(2-hydroxyethyl)-1-piperazinyl]butoxy}bibenzyl
2-[2-(1-aziridinyl)ethoxy]bibenzyl
2-[3-(1-azetidinyl)propoxy]bibenzyl
2-(3-thiomorpholinopropoxy)bibenzyl
2-[3-(4-methyl-1-piperazinyl)propoxy]bibenzyl
2-[3-(4-methylpiperidino)propoxy]bibenzyl
2-[3-(4-hydroxypiperidino)propoxy]bibenzyl
2-{2-[N-methyl-N-(2-hydroxyethyl)amino]ethoxy}-bibenzyl
2-(2-piperidinoethoxy)bibenzyl
2-(7-dimethylaminoheptyloxy)bibenzyl
2-(8-diethylaminooctyloxy)bibenzyl
3-(2-dimethylaminoethoxy)bibenzyl
3-(3-dimethylaminopropoxy)bibenzyl
3-[4-bis(2-hydroxyethyl)aminobutoxy]bibenzyl
3-[4-(1-pyrrolidinyl)butoxy]bibenzyl
3-(4-dimethylaminobutoxy)bibenzyl
4-(2-dimethylaminoethoxy)bibenzyl
4-(3-dimethylaminopropoxy)bibenzyl
4-[4-bis(2-hydroxyethyl)aminobutoxy]bibenzyl
4-[4-(1-pyrrolidinyl)butoxy]bibenzyl
4-(4-diethylaminobutoxy)bibenzyl
2-[4-(4-carboxypiperidino)butoxy]bibenzyl
2-[4-(4-methoxycarbonylpiperidino)butoxy]bibenzyl
2-[4-(4-ethoxycarbonylpiperidino)butoxy]bibenzyl
2-[4-(4-propoxycarbonylpiperidino)butoxy]bibenzyl
2-[4-(4-carbamoylpiperidino)butoxy]bibenzyl
2-[4-(4-methylcarbamoylpiperidino)butoxy]bibenzyl
2-[4-(4-dimethylcarbamoylpiperidino)butoxy]bibenzyl
2-[4-(4-ethylcarbamoylpiperidino)butoxy]bibenzyl
2-[4-(4-diethylcarbamoylpiperidino)butoxy]bibenzyl
2-[4-(4-propylcarbamoylpiperidino)butoxy]bibenzyl 2-[4-(4-dipropylcarbamoylpiperidino)butoxy]bibenzyl
2-[4-(3-carbamoylpiperidino)butoxy]bibenzyl
2-[4-(2-carboxy-1-pyrrolidinyl)butoxy]bibenzyl
2-[3-(4-carbamoylpiperidino)propoxy]bibenzyl
2-[3-(3-carbamoylpiperidino)propoxy]bibenzyl
2-[3-(4-ethoxycarbonylpiperidino)propoxy]bibenzyl
2-[3-(2-carboxy-1-pyrrolidinyl)propoxy]bibenzyl
2-[3-(3-carbamoyl-1-pyrrolidinyl)propoxy]bibenzyl
2-[2-(4-carbamoylpiperidino)ethoxy]bibenzyl
2-[2-(4-carboxypiperidino)ethoxy]bibenzyl
2-[2-(2-carboxy-1-pyrrolidinyl)ethoxy]bibenzyl
2-(2-dimethylaminoethoxy)-4'-chlorobibenzyl
2-(3-dimethylaminopropoxy)-4'-chlorobibenzyl
2-{4-[4-(2-hydroxyethyl)-1-piperazinyl]butoxy}-4'-chlorobibenzyl
2-(4-diethylaminobutoxy)-4'-chlorobibenzyl
2-(4-dimethylaminobutoxy)-4'-chlorobibenzyl
2-(4-piperidinobutoxy)-4'-chlorobibenzyl
2-[4-(1-pyrrolidinyl)butoxy]-4'-chlorobibenzyl
2-[4-(4-methylpiperidino)butoxy]-4'-chlorobibenzyl
2-[4-(4-carboxypiperidino)butoxy]-4'-chlorobibenzyl
2-[4-(4-carbamoylpiperidino)butoxy]-4'-chlorobibenzyl
2-(6-dimethylaminohexyloxy)-4'-chlorobibenzyl
2-(2-dimethylaminoethoxy)-2'-chlorobibenzyl
2-(3-dimethylaminopropoxy)-2'-chlorobibenzyl
2-(4-dimethylaminobutoxy)-2'-chlorobibenzyl
2-{4-[4-(2-hydroxyethyl)-1-piperazinyl]butoxy}-2'-chlorobibenzyl
2-(4-piperidinobutoxy)-2'-chlorobibenzyl
2-[4-(4-methylpiperidino)butoxy]-2'-chlorobibenzyl
2-[4-(1-pyrrolidinyl)butoxy]-2'-chlorobibenzyl
2-[4-(4-carboxypiperidino)butoxy]-2'-chlorobibenzyl
2-[4-(4-carbamoylpiperidino)butoxy]-2'-chlorobibenzyl
2-(6-dimethylaminohexyloxy)-2'-chlorobibenzyl
2-(3-dimethylaminopropoxy)-3'-chlorobibenzyl
2-(4-diethylaminobutoxy)-3'-chlorobibenzyl
2-[4-(4-carboxypiperidino)butoxy]-3'-chlorobibenzyl
2-[4-(4-carbamoylpiperidino)butoxy]-3'-chlorobibenzyl
2-[4-(1-pyrrolidinyl)butoxy]-3'-chlorobibenzyl
2-(2-dimethylaminoethoxy)-3',4'-dichlorobibenzyl
2-(3-dimethylaminopropoxy)-3',4'-dichlorobibenzyl
2-[4-(4-carboxypiperidino)butoxy]-3',4'-dichlorobibenzyl
2-[4-(4-carbamoylpiperidino)butoxy]-3',4'-dichlorobibenzyl
2-(2-dimethylaminoethoxy)-2',4'-dichlorobibenzyl
2-(4-dimethylaminobutoxy)-2',4'-dichlorobibenzyl
2-[4-(4-carboxypiperidino)butoxy]-2',4'-dichlorobibenzyl
2-[4-(4-carbamoylpiperidino)butoxy]-2',4'-dichlorobibenzyl
2-(3-dimethylaminopropoxy)-4'-fluorobibenzyl
2-(4-dimethylaminobutoxy)-4'-fluorobibenzyl
2-(4-diethylaminobutoxy)-4'-fluorobibenzyl
2-(4-piperidinobutoxy)-4'-fluorobibenzyl
2-[4-(4-methylpiperidino)butoxy]-4'-fluorobibenzyl
2-[4-(1-pyrrolidinyl)butoxy]-4'-fluorobibenzyl
2-[4-(4-carboxypiperidino)butoxy]-4'-fluorobibenzyl
2-[4-(4-carbamoylpiperidino)butoxy]-4'-fluorobibenzyl
2-[4-(4-dimethylcarbamoylpiperidino)butoxy]-4'-fluorobibenzyl
2-[4-(4-ethoxycarbonylpiperidino)butoxy]-4'-fluorobibenzyl
2-[4-(4-hydroxypiperidino)butoxy]-4'-fluorobibenzyl
2-(6-dimethylaminohexyloxy)-4'-fluorobibenzyl
2-(2-dimethylaminoethoxy)-2'-fluorobibenzyl
2-(4-dimethylaminobutoxy)-2'-fluorobibenzyl
2-(4-dipropylaminobutoxy)-2'-fluorobibenzyl
2-[4-(4-carboxypiperidino)butoxy]-2'-fluorobibenzyl
2-[4-(4-carbamoylpiperidino)butoxy]-2'-fluorobibenzyl
2-[4-(1-pyrrolidinyl)butoxy]-2'-fluorobibenzyl
2-[4-4-(2-hydroxyethyl)-1piperazinyl]butoxy-2'-fluorobibenzyl
2-(3-dimethylaminopropoxy)-3'-fluorobibenzyl
2-[4-4-(2-hydroxyethyl)-1-piperazinyl]butoxy-3'-fluorobibenzyl
2-[4-(4-carboxypiperidino)butoxy]-3'-fluorobibenzyl
2-[4-(4-carbamoylpiperidino)butoxy]-3'-fluorobibenzyl
2-(2-dimethylaminoethoxy)-2'-methoxybibenzyl
2-(4-dimethylaminobutoxy)-2'-methoxybibenzyl
2-(4-piperidinobutoxy)-2'-methoxybibenzyl
2-[4-(1-pyrrolidinyl)butoxy]-2'-ethoxybibenzyl
2-{4-[4-(2-hydroxyethyl)-1-piperazinyl]butoxy}-2'-methoxybibenzyl
2-(4-dimethylaminobutoxy)-3'-methoxybibenzyl
2-{4-[4-(2-hydroxyethyl)-1-piperazinyl]butoxy}-3'-methoxybibenzyl
2-(3-dimethylaminopropoxy)-2'-ethoxybibenzyl
2-(4-dimethylaminobutoxy)-2'-ethoxybibenzyl
2-(4-diethylaminobutoxy)-2'-ethoxybibenzyl
2-(2-dimethylaminoethoxy)-2'-hydroxybibenzyl
2-(4-dimethylaminobutoxy)-2'-hydroxybibenzyl
2-(2-dimethylaminoethoxy)-2'-carboxybibenzyl
2-(4-dimethylaminobutoxy)-2'-carboxybibenzyl
2-{4-[4-(2-hydroxyethyl)-1-piperazinyl]butoxy}-2'-carboxybibenzyl
2-(2-dimethylaminoethoxy)-2'-methoxycarbonylbibenzyl
2-(4-dimethylaminobutoxy)-2'-methoxycarbonylbibenzyl
2-(4-dimethylaminobutoxy)-3'-methoxycarbonylbibenzyl
2-(3-dimethylaminopropoxy)-3'-carboxybibenzyl
2-(4-dimethylaminobutoxy)-4'-carboxybibenzyl
2-(4-dimethylaminobutoxy)-4'-methoxycarbonylbibenzyl
2-(4-dimethylaminobutoxy)-2'-methylbibenzyl
2-(4-piperidinobutoxy)-2'-methylbibenzyl
2-[4-(1-pyrrolidinyl)butoxy]-2'-ethylbibenzyl
2-[4-(4-carbamoylpiperidino)butoxy]-2'-methylbibenzyl
2-[4-(4-methyl-1-piperazinyl)butoxy]-2'-methylbibenzyl
2-(4-diethylaminobutoxy)-2'-propylbibenzyl
2-(3-dimethylaminopropoxy)-3'-methylbibenzyl
2-[4-(4-carboxypiperidino)butoxy]-3'-ethylbibenzyl
2-(4-dimethylaminobutoxy)-4'-methylbibenzyl
2-(3-dimethylaminopropoxy)-4'-dimethylaminobibenzyl
2-[4-(4-carbamoylpiperidino)butoxy]-4'-dimethylaminobibenzyl
2-[4-4-(2-hydroxyethyl)-1-piperazinyl]butoxy-4'-dimethylaminobibenzyl
2-(3-dimethylaminopropoxy)-5-chlorobibenzyl
2-(4-piperidinobutoxy)-5-chlorobibenzyl
2-4-(4-methylpiperidino)butoxy-5-chlorobibenzyl
2-(3-dimethylaminopropoxy)-5-fluorobibenzyl
2-[4-(4-carbamoylpiperidino)butoxy]-5-fluorobibenzyl 2-(4-dimethylaminobutoxy)-3-methoxybibenzyl
2-(4-diethylaminobutoxy)-3-ethoxybibenzyl
2-[4-(4-carboxypiperidino)butoxy]-3-propoxybibenzyl
2-[4-bis(2-hydroxyethyl)aminobutoxy]-3-methoxybibenzyl
2-(4-dimethylaminobutoxy)-5-methoxybibenzyl The pharmaceutically acceptable acid addition salts of the above compounds are, of course, also included within the scope of this invention.

It will be understood that the term "pharmaceutically acceptable acid addition salts" as used herein is intended to include non-toxic salts of the compounds of this invention with an anion.

Representative of such salts are hydrochlorides, hydrobromides, sulfates, phosphates, nitrates, acetates, fumarate, succinates, adipates, propionates, tartrates, maleates, citrates, benzoates, toluenesulfonates and methanesulfonates.

Of the compounds of this invention, it will be understood that the following compounds are most preferred due to their high level of ability to inhibit the platelet aggregation.
2-(2-dimethylaminoethoxy)bibenzyl
2-(4-dimethylaminobutoxy)bibenzyl
2-{4-[4-(2-hydroxyethyl)-1-piperazinyl]butoxy}bibenzyl
2-(4-diethylaminobutoxy)bibenzyl
2-[4-(4-carbamoylpiperidino)butoxy]bibenzyl
2-(4-dimethylaminobutoxy)-3'-methoxybibenzyl
2-(4-piperidinobutoxy)-2'-chlorobibenzyl
2-[4-(4-carbamoylpiperidino)butoxy]-4'-fluorobibenzyl
2-(3-dimethylaminopropoxy)-4'-dimethylaminobibenzyl
2-(3-dimethylaminopropoxy)-5-chlorobibenzyl The above compounds are intended only to illustrate the typical compounds of this invention, and the above listing is not to be construed as limiting the scope of the invention. For the preparation of the compounds of this invention, various methods can be employed depending upon the particular starting materials and/or intermediates involved. Successful preparation of these compounds is possible by way of several synthetic routes which are outlined below.

The compounds of this invention are prepared by reacting an (omega-halogenoalkoxy)bibenzyl of the formula (III):

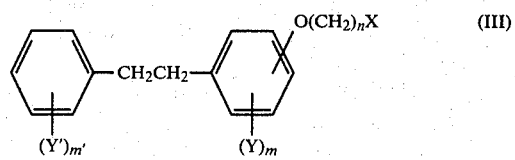

wherein X is halogen; and Y, Y', m, m' and n are as defined herein above, with an amine of the formula (IV):

R—H  (IV)

wherein R is as defined herein above.

The (omega-halogenoalkoxy)bibenzyl starting materials which are represented by Formula III above can be prepared by reacting a hydroxybibenzyl of the formula (V):

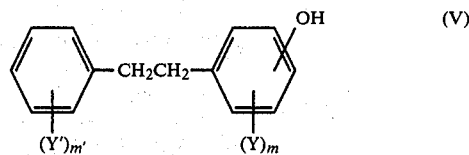

wherein Y, Y', m and m' are as defined herein above, with an α,ω-dihalogenoalkane of the formula (VI):

$X(CH_2)_nX$  (VI)

wherein X is halogen, and n is as defined herein above, in the presence of an alkali.

The hydroxybibenzyl which can be represented by the formula (V) is prepared by hydrogenolysis of a carbinol obtained by Grignard reaction between a benzyl chloride of the formula (VII):

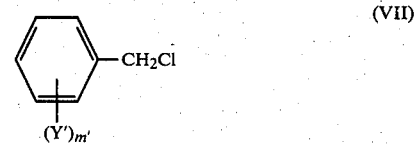

wherein Y' and m' are as defined herein above, and a hydroxybenzaldehyde of the formula (VIII):

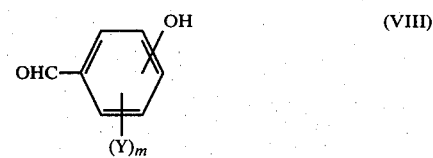

wherein Y and m are as defined herein above (See Ann. 433 237 (1923) and Bull. Chem. Soc. Japan 33 681 (1960)).

The hydrogenolysis is effected in the presence of an acid and a catalyst, e.g., palladium on carbon catalyst.

The alternate route leading to the hydroxybibenzyl comprises hydrogenating in the presence of a palladium catalyst a stilbene obtained by Wittig reaction between a substituted benzaldehyde of the formula (IX):

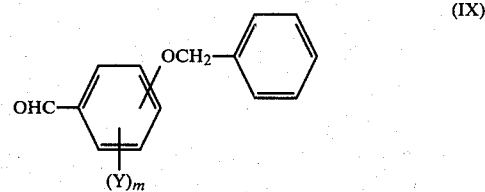

wherein Y and m are as defined herein above, and a triphenylphosphonium salt of the benzyl chloride of the formula (VII) (See J. Med. Chem. 20 1557 (1977) and Chem. Pharm. Bull. 25 706 (1977)).

The amine (IV) reacts with the equimolar amount of the (omega-halogenoalkoxy)bibenzyl (III). However, the use of the excess amine accelerates the reaction. Normally, the amount of the amine to be employed is in the range of 1 to 100 moles per mole of the (omega-halogenoalkoxy)bibenzyl.

The reaction can be carried out without an added solvent.

However, the use of a reaction-inert solvent makes a homogenous reaction possible. Examples of such solvents are water, dioxane, tetrahydrofuran, dimethylformamide, lower aliphatic alcohols and the mixtures thereof. The reaction temperature is not critical, but normally ranges from room temperature to 150° C. The reaction time varies widely with the reaction temperature and the reactivity of the starting materials, but normally is in the range of from 10 minutes to 40 hours.

The presence of bases which neutralize a hydrogen halide formed in the course of the reaction accelerates the reaction.

Examples of such bases are inorganic bases such as potassium hydroxide, sodium hydroxide, potassium carbonate, sodium carbonate and the like; and tertiary amines such as pyridine, triethylamine and the like.

The amount of the base to be employed is normally in the range of 1 to 5 moles per mole of the (omega-halogenoalkoxy)bibenzyl. When the base is absent, the (omega-aminoalkoxy)bibenzyl reacts further with a hydrogen halide formed during the reaction, and is converted to the acid addition salts thereof.

A desired acid addition salt may be conveniently prepared by removing the excess amine and the solvent, converting an acid addition salt of an (omega-aminoalkoxy)bibenzyl to its free form by the addition of an aqueous solution of a strong base such as sodium hydroxide, potassium hydroxide or the like, extracting it with a solvent such as ether, chloroform, benzene or the like, and then neutralizing it with a desired acid. An alternate route leading to a desired acid addition salt comprises desalting a salt of a carboxylic acid derivative by the treatment of an ion exchange resin, dissolving it into a lower alcohol, e.g., methanol and ethanol, and then adding a desired acid.

Another method for preparing the compounds of this invention comprises reacting an alkali metal salt of a hydroxybibenzyl of the formula (X):

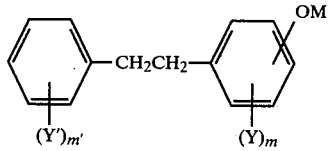 (X)

wherein M is an alkali metal; and Y, Y', m and m' are as defined herein above, with an omega-halogenoalkylamine of the formula (XI):

 (XI)

wherein X is halogen; and R and n are as defined herein above.

The reaction can be carried out in a hydrocarbon solvent such as toluene, xylene or the like or an aprotic solvent such as dimethylformamide at a temperature up to the boiling point of the solvent.

The amount of the omega-halogenoalkylamine (XI) to be employed is in the range of 1 to 5 moles per mole of the hydroxybibenzyl (V). The reaction time varies with the reaction temperature, but normally is in the range of 5 to 120 minutes.

The same post-treatment as in the aforesaid method yields the (omega-aminoalkoxy)bibenzyl or its acid addition salt, which can be purified by recrystallization from a suitable solvent such as alcohol-ether.

An (omega-aminoalkoxy)bibenzyl wherein $R_3$, $R_4$ or $R_5$ is alkoxycarbonyl is prepared by esterification of the corresponding (omega-aminoalkoxy)biphenyl wherein $R_3$, $R_4$ or $R_5$ is carboxyl at a temperature of 50° to 150° C. for about 1 to 10 hours in an alcohol ($R_3OH$, $R_4OH$ or $R_5OH$) with the use of an acid catalyst.

An (omega-aminoalkoxy)bibenzyl wherein $R_3$, $R_4$ or $R_5$ is carboxyl is converted to the corresponding acid halogenide by the action of a halogenating agent, e.g., thionyl chloride or phosphorous pentachloride, either in the absence or presence of a solvent, e.g., phosphorous oxychloride, at a temperature of 20° to 100° C. Amidation of the acid halogenide with an amine of the formula (XII):

 (XII)

wherein $R_6$ and $R_7$ are as defined herein above, is carried out in a solvent, e.g., water, tetrahydrofuran, dioxane or chloroform in the presence of a basic catalyst at a temperature of −20° to 50° C. for 0.5 to 5 hours.

Pharmacological testing of the (omega-aminoalkoxy)bibenzyls of this invention has demonstrated that they possess anti-coagulant activity, especially activity against blood platelet aggregation, and are suitable for use in the cure and prevention of thrombosis. Their activity against blood platelet aggregation can be demonstrated by an increase or decrease in platelet aggregation value caused by the administration of the compounds of this invention to rabbits.

Evaluation of the compounds of this invention for their activity against platelet aggregation was carried out according to a turbidometric method described by G. V. R. Born, Nature 194 927 (1962). Platelet aggregation was measured using platelet-rich plasma prepared from citrated blood which was collected from a carotid artery of male white rabbits of Japanese native kind. A suspension of collagen (bovine Achilles tendon collagen, Sigma) in saline was used to cause platelet aggregation. The aggregation of rabbit blood platelet was induced by adding the suspension of collagen to give 10 to 15 μg collagen per milliliter. At this time, the tests were conducted at 37° C. at levels of $4 \times 10^5$ platelet/mm$^3$. A solution of compounds of this invention in saline was added to the platelet-rich plasma. After three minutes of preincubation with the platelet-rich plasma, collagen was added to cause platelet aggregation. Percent inhibition was calculated by comparison with controls.

Using the above procedure, the compounds of this invention were compared to aspirin.

The concentration of the compound in micromoles inhibiting platelet aggregation by 50 percent ($I_{50}$) and $LD_{50}$ which was calculated by Litchfield-Wilcoxon method are shown in Table 1.

The compounds of this invention can be administered by any means that effects inhibiting blood platelet aggregation in warm-blooded animals.

For example, administration can be parenterally, subcutaneously, intravenously, intramuscularly, or intraperitoneally. Alternatively or concurrently, administration can be by the oral route. The dosage administered will be dependent upon the age, health and weight of the recipient, kind of concurrent treatment if any, frequency of treatment, and the nature of the effect desired. Generally, a daily dosage of active ingredient compound will be from about 0.5 to 50 mg per kg of body weight. Normally, from 1 to 30 mg per kg per day, in one or more applications per day is effective to obtain the desired result.

The compound of this invention can be employed in dosage forms such as tablets, capsules, powder packets, or liquid solutions, or elixirs, for oral administration, or sterile liquid formulations such as solutions or suspensions for parenteral use. In such compositions, besides the active ingredient of this invention, the composition will contain a solid or liquid non-toxic pharmaceutical carrier for the active ingredient. In one embodiment of a composition, the solid carrier can be a capsule of the ordinary gelatin type. In another embodiment, the active ingredient can be tableted with or without adjuvants, or put into powder packets. These capsules, tablets and powders will generally constitute from about 5% to about 95% and preferably from 25% to 90% by weight of active ingredient. These dosage forms preferably contain from about 5 to about 500 mg of active ingredient, with from about 25 to about 250 mg being most preferred.

The pharmaceutical carrier can be a sterile liquid such as water and oils, including those of petroleum, animal, vegetable or synthetic origin, such as peanut oil, soybean oil, mineral oil, sesame oil, and the like.

In general, water saline, aqueous dextrose and related sugar solutions, and glycols such as propylene glycol and polyethylene glycol are preferred liquid carriers, particularly for injectible solutions such as saline will ordinarily contain from about 0.5% to 20% and preferably about 1 to 10% by weight of the active ingredient.

As mentioned above, oral administration can be in a suitable suspension or syrup, in which the active ingredient normally will constitute from about 0.5 to 10% by weight. The pharmaceutical carrier in such composition can be a watery vehicle such as an aromatic water, a syrup or a pharmaceutical mucilage.

Having generally described the invention, a more complete understanding can be obtained by reference to certain specific examples, which are included for purposes of illustration only and are not intended to be limiting unless otherwise specified.

EXAMPLE 1

A solution of 3.19 g of 2-(3-bromopropoxy)bibenzyl in 60 ml of ethanol and 30 ml of 50% dimethylamine aqueous solution was allowed to stand at room temperature for 20 hours. Ethanol and excess dimethylamine were distilled in vacuo, 2 N-NaOH aqueous solution was added, and the reaction product was extracted with isopropyl ether. The isopropyl ether solution was dried over anhydrous sodium sulfate, and then 20% ethanolic hydrogen chloride solution was added. The resulting precipitate was collected by filtration and recrystallized from ethanol-ether to give 2.88 g (90% yield) of 2-(3-dimethylaminopropoxy)bibenzyl hydrochloride, m. p. 134°–136° C.

Analysis-Calcd. for $C_{19}H_{25}NO.HCl$ (percent): C, 71.34; H, 8.19; N, 4.38 Found (percent): C, 71.20; H, 8.23; N, 4.30.

EXAMPLE 2

A solution of 3.33 g of 2-(4-bromobutoxy)bibenzyl and 6 g of piperazine in 20 ml of ethanol was heated under reflux for 10 hours. Ethanol and excess piperazine were distilled in vacuo, 2 N-NaOH aqueous solution was added, and the reaction product was extracted with benzene. The benzene solution was dried over anhydrous sodium sulfate and distilled in vacuo. The residue was dissolved in ethyl ether and then 20% ethanolic hydrogen chloride solution was added. The resulting precipitate was collected by filtration and recrystallized from ethanol-ether to give 3.09 g (75% yield) of 2-[4-(1-piperazinyl)butoxy]bibenzyl dihydrochloride, m. p. 134°–140° C.

Analysis-Calcd. for $C_{22}H_{30}N_2O.2HCl$ (percent): C, 64.23; H, 7.84; N, 6.81 Found (percent): C, 63.99; H, 7.51; N, 6.77.

EXAMPLE 3

To a suspension of 1.0 g of lithium hydride in 30 ml of toluene was added dropwise a solution of 3.96 g of 2-hydroxybibenzyl in 30 ml of toluene at room temperature over 5 minutes. The mixture was heated under reflux for 30 minutes, a solution of 6.45 g of 2-chloro-N,N-dimethylethylamine in 20 ml of toluene added dropwise under reflux over 5 minutes and then reflux was continued for an additional 2 hours. The reaction mixture was cooled to room temperature, and to this was added 50 ml of water. The toluene layer was separated, washed twice with water, dried over anhydrous sodium sulfate and then the toluene distilled off in vacuo. The residue was dissolved in ethyl ether, and then 20% ethanolic hydrogen chloride solution was added. The resulting precipitate was collected by filtration and recrystallized from ethanol-ether to give 5.81 g (95% yield) of 2-(2-dimethylaminoethoxy)bibenzyl hydrochloride, m. p. 172°–173° C.

Analysis-Calcd. for $C_{18}H_{23}NO.HCl$ (percent): C, 70.69; H, 7.91; N, 4.58 Found (percent): C, 70.49; H, 7.68; N, 4.62.

EXAMPLE 4

To a solution of 1.9 g of 4-piperidinecarboxylic acid and 1.2 g of sodium hydroxide in 50 ml of ethanol was added dropwise 5 g of 2-(4-bromobutoxy)bibenzyl under reflux. Reflux was continued for an additional 30 minutes, and the reaction mixture was concentrated in vacuo to remove the solvent. To the residue was added water and then the mixture was adjusted to pH 2-3 with 2 N-hydrochloric acid. The product was extracted with chloroform. The extract from chloroform was washed with saturated sodium chloride solution and dried over anhydrous sodium sulfate. The solvent was distilled off in vacuo to give 4.8 g (77% yield) of 2-[4-(4-carboxypiperidino)butoxy]bibenzyl hydrochloride, m. p. 155°–162° C.

Analysis-Calcd. for $C_{24}H_{31}NO_3.HCl$ (percent): C, 68.97; H, 7.72; N, 3.35 Found (percent): C, 68.69; H, 7.83; N, 3.11.

EXAMPLE 5

A solution of 2 g of 2-(2-bromoethoxy)bibenzyl and 1.7 g of 4-piperidinecarboxamide in 20 ml of tetrahydrofuran and 10 ml of water was stirred at 70° C. for 10 hours. The reaction mixture was concentrated and to the residue was added 1 N NaOH aqueous solution. The resultant crystals were filtered, washed well with water and then recrystallized from ethanol to give 1.9 g (82% yield) of 2-[2-(4-carbamoylpiperidino)ethoxy]bibenzyl, m. p. 60°–63° C.

Analysis-Calcd. for $C_{22}H_{28}N_2O_2$ (percent): C, 74.97; H, 8.01; N, 7.95 Found (percent): C, 74.81, H, 7.90; N, 7.91.

EXAMPLE 6

To a solution of 3 g of 2-[4-(4-carboxypiperidino)butoxy]bibenzyl hydrochloride in 30 ml of ethanol was added dropwise 0.9 g of thionyl chloride. The reaction mixture was stirred for one hour, heated under reflux for 30 minutes, concentrated in vacuo and then recrystallized from ethanolether to give 2.8 g (87% yield) of 2-[4-(4-ethoxycarbonylpiperidino)butoxy]bibenzyl hydrochloride, m. p. 84°–87° C.

Analysis-Calcd. for $C_{26}H_{35}NO_3.HCl$ (percent): C, 70.01, H, 8.14; N, 3.14 Found (percent): C, 69.82; H, 8.01; N, 3.33.

EXAMPLE 7

To 6.0 g of 2-[4-(4-carboxypiperidino)butoxy]bibenzyl hydrochloride was added dropwise 15 ml of thionyl chloride with stirring. The reaction mixture was stirred at room temperature for 3 hours. As the reaction proceeded the reaction mixture became homogenous. Upon completion of the reaction, anhydrous ether was added and the resultant oily product was washed well twice or three times with anhydrous ether. To the washed oil was added anhydrous ether and the mixture was allowed to stand yielding crystalline 2-[4-(4-chlorocarbonylpiperidino)butoxy]bibenzyl hydrochloride which was sufficiently dried for use in the subsequent reaction. To a solution of 10 ml of 50% aqueous dimethylamine solution and 10 ml of tetrahydrofuran cooled in an ice-salt bath was quickly added 1.5 g of crystalline 2-[4-(4-chlorocarbonylpiperidino)butoxy]bibenzyl hydrochloride with stirring. The mixture was allowed to react for 1.5 hours and then concentrated. To the concentrate was added 2N-NaOH aqueous solution and the product was extracted with ether. The extract from ether was washed with saturated sodium chloride solution and dried over anhydrous sodium sulfate. To the ether solution was added 20% ethanolic hydrogen chloride to yield a precipitate. Recrystallization from etherethanol gave 1.2 g (78% yield) of 2-[4-(4-dimethylcarbamoylpiperidino)butoxy]bibenzyl hydrochloride, m. p. 139°–160° C.

Analysis-Calcd. for $C_{26}H_{36}N_2O_2.HCl$ (percent): C, 70.17; H, 8.38; N, 6.29 Found (percent): C, 69.79; H, 8.23; N, 6.41.

EXAMPLE 8

A solution of 3.0 g of 2-(4-bromobutoxy)-2'-chlorobibenzyl in 15 ml of 50% aqueous dimethylamine solution and 15 ml of tetrahydrofuran was stirred at room temperature for 5 hours. The reaction mixture was concentrated and to the concentrate was added 2N-NaOH solution. The product was extracted with ether, washed well with saturated sodium chloride solution and then dried over anhydrous sodium sulfate. To the ether solution was added 20% ethanolic hydrogen chloride to yield white crystals. Recrystallization from ethanol-ether gave 2.8 g (93% yield) of 2-(4-dimethylaminobutoxy)-2'-chlorobibenzyl hydrochloride, m. p. 122°–123° C.

Analysis-Calcd. for $C_{20}H_{26}NCl0.HCl$ (percent): C, 65.22; H, 7.39; N, 3.80 Found (percent): C, 65.51; H, 7.09; N, 3.81.

EXAMPLE 9

A solution of 3.0 g of 2-(4-bromomethoxy)-2'-methoxybibenzyl and 2.3 g of 4-(2-hydroxyethyl) piperazine in 30 ml of tetrahydrofuran and 10 ml of water was stirred at 70° C. for 8 hours. Upon completion of the reaction, the same treatment as in Example 8 was conducted. Recrystallization from methanol-ether gave 2.7 g (72% yield) of 2-4-[4-(2-hydroxyethyl)-1-piperazinyl]butoxy-2'-methoxybibenzyl dihydrochloride, m. p. 188°–191° C.

Analysis-Calcd. for $C_{25}H_{36}N_2O_3.2HCl$ (percent): C, 61.85; H, 7.89; N, 5.77 Found (percent): C, 61.94; H, 8.19; N, 5.61.

EXAMPLE 10

To a solution of 2.5 g of 2-hydroxy-3',4'-dichlorobibenzyl in 10 ml of dimethylformamide was added 0.23 g of sodium hydride under cooling. The mixture was stirred for 30 minutes and to this was added dropwise 2.2 g of 3-dimethylaminopropyl chloride. The reaction mixture was warmed to about 60° C. and then stirred for 5 hours. Upon completion of the reaction, 2N-NaOH aqueous solution was added, and the product was extracted with ether. The ether extract was washed well with saturated sodium chloride solution, dried over anhydrous sodium sulfate and then distilled in vacuo to sufficiently remove ether and a small amount of the remaining 3-dimethylaminopropyl chloride. The resultant residue was dissolved in ether and then 20% ethanolic hydrogen chloride was added to yield a precipitate. Recrystallization from ethanol-ether gave 2.6 g (71% yield) of 2-(3-dimethylaminopropoxy)-3',4'-dichlorobibenzyl hydrochloride, m. p. 136°–137° C.

Analysis-Calcd. for $C_{19}H_{23}NCl_2O.HCl$ (percent) C, 58.70; H, 6.22; N, 3.60 Found (percent): C, 58.65; H, 6.11; N, 3.53.

Various other (omega-aminoalkoxy)bibenzyls were synthesized in accordance with the procedures of the above examples. The results, including those of the above examples, are summarized in Table 1.

TABLE 1

Compound:

$Y_1'$—(phenyl with $Y_2'$)—$CH_2CH_2$—(phenyl with $Y_1$, $Y_2$, $O(CH_2)_nR$)

| Sample No. | Position of —O(CH$_2$)$_n$R group | n | R | Y$_1$ | Y$_1'$ | Y$_2$ | Y$_2'$ | Addition moiety | Preparation process (Ex. No.) | m.p. (°C.) | Elementary analysis Upper: Calcd. (%) Lower: Found (%) C | H | N | I$_{50}$ (μMol) | ID$_{50}$ (mg/kg i.p. in mice) |
|---|---|---|---|---|---|---|---|---|---|---|---|---|---|---|---|
| 1 | 2 | 2 | –N(CH$_3$)$_2$ | H | H | H | H | HCl | 3 | 172–3 | 70.69 / 70.49 | 7.91 / 7.68 | 4.58 / 4.62 | 0.6 | 165 |
| 2 | " | 3 | –N(CH$_3$)$_2$ | " | " | " | " | " | 1 | 134–6 | 71.34 / 71.20 | 8.19 / 8.23 | 4.38 / 4.30 | 0.6 | — |
| 3 | " | 4 | –N(CH$_3$)$_2$ | " | " | " | " | " | 1 | 113–8 | 71.94 / 71.69 | 8.45 / 8.55 | 4.20 / 4.16 | 0.6 | 215 |
| 4 | " | 5 | –N(CH$_3$)$_2$ | " | " | " | " | " | 1 | 94–6 | 72.49 / 72.34 | 8.69 / 8.53 | 4.03 / 3.94 | 0.8 | 205 |
| 5 | " | 6 | –N(CH$_3$)$_2$ | " | " | " | " | " | 1 | Powder | 73.00 / 72.96 | 8.91 / 8.73 | 3.87 / 3.90 | 1 | — |
| 6 | " | 4 | –N(H)(CH$_3$) | " | " | " | " | " | 1 | 106–111 | 71.34 / 71.11 | 8.19 / 8.19 | 4.38 / 4.05 | 7 | — |
| 7 | " | 4 | –N(CH$_3$)(CH$_2$CH$_2$CH$_2$CH$_3$) | " | " | " | " | " | 1 | 90–93 | 73.47 / 73.20 | 9.12 / 9.00 | 3.73 / 3.61 | 3 | — |

TABLE 1-continued

Compound:

Y₁'—[benzene ring]—CH₂CH₂—[benzene ring with Y₁ and O(CH₂)ₙR]
Y₂'—

| Sample No. | Position of —O(CH₂)ₙR group | n | R | Y₁ | Y₁' | Y₂' | Addition moiety | Preparation process (Ex. No.) | m.p. (°C.) | Elementary analysis Upper: Calcd. (%) / Lower: Found (%) C | H | N | I₅₀ (μ Mol) | ID₅₀ (mg/kg i.p. in mice) |
|---|---|---|---|---|---|---|---|---|---|---|---|---|---|---|
| 8 | " | 4 | —N(CH₃)(CH₂CH₂OH) | " | " | " | " | 2 | Powder | 69.30 / 69.00 | 8.31 / 8.30 | 3.85 / 3.55 | 2 | — |
| 9 | " | 4 | piperidino | " | " | " | " | 2 | 125–7 | 73.87 / 73.32 | 8.63 / 8.61 | 3.75 / 3.70 | 1 | — |
| 10 | " | 4 | morpholino | " | " | " | " | 2 | 125–130 | 70.29 / 70.20 | 8.04 / 8.11 | 3.73 / 3.73 | 10 | — |
| 11 | " | 4 | piperazino (NH) | " | " | " | 2HCl | 2 | 134–140 | 64.23 / 63.99 | 7.84 / 7.51 | 6.81 / 6.77 | 2 | — |
| 12 | " | 4 | pyrrolidino | " | " | " | HCl | 2 | 110–114 | 73.41 / 73.20 | 8.40 / 8.12 | 3.89 / 3.69 | 0.7 | — |
| 13 | " | 4 | 4-(2-hydroxyethyl)piperazino | " | " | " | 2HCl | 2 | 177–180 | 63.29 / 63.18 | 7.97 / 7.77 | 6.15 / 5.97 | 3 | — |
| 14 | " | 4 | —N(CH₂CH₂OH)₂ | " | " | " | HCl | 2 | Powder | 67.07 / 67.35 | 8.19 / 8.20 | 3.56 / 3.26 | 5 | — |

TABLE 1-continued

Compound:

$$\text{Y}_1'\text{-C}_6\text{H}_3\text{-Y}_2\text{-CH}_2\text{CH}_2\text{-C}_6\text{H}_3(\text{Y}_1)(\text{O(CH}_2)_n\text{R})$$

| Sample No. | Position of —O(CH$_2$)$_n$R group | n | R | Y$_1$ | Y$_1'$ | Y$_2'$ | Addition moiety | Preparation process (Ex. No.) | m.p. (°C.) | Elementary analysis Upper: Calcd. (%) Lower: Found (%) C | H | N | I$_{50}$ (μMol) | ID$_{50}$ (mg/kg i.p. in mice) |
|---|---|---|---|---|---|---|---|---|---|---|---|---|---|---|
| 15 | " | 2 | —N(C$_2$H$_5$)$_2$ | | | | " | 3 | 170–170.5 | 71.94 / 71.57 | 8.45 / 8.55 | 4.19 / 3.99 | 0.5 | — |
| 16 | " | 3 | —N(C$_2$H$_5$)$_2$ | | | | " | 2 | 140–2 | 72.49 / 72.23 | 8.69 / 8.49 | 4.03 / 3.85 | 0.5 | 187 |
| 17 | " | 4 | —N(C$_2$H$_5$)$_2$ | | | | " | 2 | Powder | 73.91 / 73.65 | 9.30 / 9.25 | 3.59 / 3.60 | 0.8 | — |
| 18 | " | 5 | —N(C$_2$H$_5$)$_2$ | | | | " | 2 | 122–129 | 73.00 / 73.15 | 8.91 / 8.95 | 3.87 / 3.99 | 1 | — |
| 19 | " | 6 | —N(C$_2$H$_5$)$_2$ | | | | " | 2 | 114–6 | 73.47 / 73.73 | 9.12 / 9.34 | 3.73 / 3.65 | 1 | — |
| 20 | 4 | 3 | —N(CH$_3$)$_2$ | | | | " | 3 | 196–7 | 71.34 / 71.35 | 8.19 / 8.21 | 4.38 / 4.34 | 2 | — |
| 21 | " | 4 | —N(CH$_3$)$_2$ | | | | " | 1 | 169–171 | 71.91 / 71.87 | 8.45 / 8.35 | 4.20 / 4.08 | 2 | — |

TABLE 1-continued

Compound: structure with CH₂CH₂ linker between two phenyl rings bearing Y₁/Y₂/Y₁'/Y₂' substituents and an O(CH₂)ₙR group

| Sample No. | Position of —O(CH₂)ₙR group | n | R | Y₁ | Y₁' | Y₂' | Addition moiety | Preparation process (Ex. No.) | m.p. (°C.) | Elementary analysis Upper: Calcd. (%) Lower: Found (%) C | H | N | I₅₀ (μ Mol) | ID₅₀ (mg/kg i.p. in mice) |
|---|---|---|---|---|---|---|---|---|---|---|---|---|---|---|
| 22 | 2 | 4 | piperidine-CO₂H | " | " | " | " | 4 | 155–162 | 68.97 / 68.69 | 7.72 / 7.83 | 3.35 / 3.11 | 5.5 | 500 |
| 23 | " | 4 | piperidine-CO₂Et | " | " | " | " | 6 | 84–87 | 70.01 / 69.82 | 8.14 / 8.01 | 3.14 / 3.33 | — | — |
| 24 | " | 4 | piperidine-CONH₂ | " | " | " | — | 5 | 106 | 75.75 / 75.97 | 8.48 / 8.51 | 7.36 / 7.13 | 1.5 | 500 |
| 25 | " | 2 | piperidine-CONH₂ | " | " | " | — | 5 | 60–63 | 74.97 / 74.81 | 8.01 / 7.90 | 7.95 / 7.91 | 2.5 | — |
| 26 | " | 4 | piperidine-CON(CH₃)₂ | " | " | " | HCl | 7 | 159–160 | 70.17 / 69.79 | 8.38 / 8.23 | 6.29 / 6.41 | 3 | — |
| 27 | " | 4 | piperidine-CONHEt | " | " | " | " | 7 | 125–130 | 70.17 / 70.01 | 8.38 / 8.59 | 6.29 / 6.03 | 2.5 | — |

TABLE 1-continued

Compound structure: two phenyl rings connected by CH₂CH₂, with substituents Y₁, Y₁', Y₂, Y₂', and O(CH₂)ₙR group.

| Sample No. | Position of —O(CH₂)ₙR group | n | R | Y₁ | Y₁' | Y₂ | Y₂' | Addition moiety | Preparation process (Ex. No.) | m.p. (°C.) | Elementary analysis Calcd. (%) / Found (%) C | H | N | I₅₀ (μMol) | ID₅₀ (mg/kg i.p. in mice) |
|---|---|---|---|---|---|---|---|---|---|---|---|---|---|---|---|
| 28 | " | 4 | COOH / pyrrolidine-2-yl | Y₁ | " | " | " | " | 4 | 118-124 | 68.39 / 68.63 | 7.49 / 7.34 | 3.47 / 3.37 | — | — |
| 29 | " | 4 | CONH₂ / piperidin-3-yl | " | " | " | " | — | 5 | 114-118 | 69.13 / 68.97 | 7.98 / 7.34 | 6.72 / 6.91 | 1.4 | 270 |
| 30 | " | 3 | CONH₂ / piperidin-4-yl | " | " | " | " | — | 5 | 85-87 | 75.38 / 75.09 | 8.25 / 8.11 | 7.64 / 7.37 | 2 | — |
| 31 | " | 2 | —N(CH₃)₂ | " | 2'-OCH₃ | " | " | HCl | 10 | 228-229 | 67.94 / 68.24 | 7.80 / 7.96 | 4.17 / 4.21 | 0.6 | — |
| 32 | " | 4 | —N(CH₃)₂ | " | 2'-OCH₃ | " | " | " | 8 | 150-154 | 69.31 / 69.23 | 8.31 / 8.54 | 3.85 / 3.68 | 0.9 | 250 |
| 33 | " | 4 | piperazine-NCH₂CH₂OH | " | 2'-OCH₃ | " | " | 2HCl | 9 | 188-191 | 61.85 / 61.94 | 7.89 / 8.19 | 5.77 / 5.61 | — | — |
| 34 | " | 4 | —N(CH₃)₂ | " | 3'-OCH₃ | " | " | HCl | 8 | 101-102 | 69.31 / 69.22 | 8.31 / 8.39 | 3.85 / 3.69 | 0.55 | 200 |
| 35 | " | 4 | piperazine-NCH₂CH₂OH | " | 3'-OCH₃ | " | " | 2HCl | 9 | 170-175 | 61.85 / 61.98 | 7.89 / 7.75 | 5.77 / 6.01 | 1.2 | — |
| 36 | " | 4 | —N(CH₃)₂ | " | 2'-OCH₂CH₃ | " | " | HCl | 8 | 184-188 | 69.91 / 70.13 | 8.53 / 8.81 | 3.71 / 3.54 | — | — |
| 37 | " | 4 | —N(CH₂CH₃)₂ | " | 2'-OCH₂CH₃ | " | " | " | 9 | 99-103 | 71.00 / 70.75 | 8.94 / 8.59 | 3.45 / 3.51 | 1.0 | — |

TABLE 1-continued

Compound

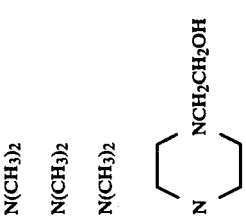

| Sample No. | Position of —O(CH₂)ₙR group | n | R | Y₁' | Y₂' | Y₁ | Y₂ | Addition moiety | Preparation process (Ex. No.) | m.p. (°C.) | Elementary analysis Upper: Calcd. (%) Lower: Found (%) C | H | N | I₅₀ (μ Mol) | ID₅₀ (mg/kg i.p. in mice) |
|---|---|---|---|---|---|---|---|---|---|---|---|---|---|---|---|
| 38 | " | 4 | —N(CH₃)₂ | | | 2'-OH | | " | 8 | 126–129 | 68.65 69.00 | 8.07 8.08 | 4.00 3.92 | 0.9 | 167 |
| 39 | " | 2 | —N(CH₃)₂ | | | 2'-COOH | | " | 10 | 158–166 | 65.23 64.91 | 6.91 6.83 | 4.00 3.79 | — | — |
| 40 | " | 4 | —N(CH₃)₂ | | | 2'-COOH | | " | 8 | 128–131 | 66.74 66.72 | 7.47 7.14 | 3.71 3.56 | — | — |
| 41 | " | 2 | —N(CH₃)₂ | | | 2'-CO₂CH₃ | | " | 10 | 160–164 | 66.02 66.30 | 7.20 7.19 | 3.85 3.76 | 0.5 | 130 |
| 42 | " | 4 | —N(CH₃)₂ | | | 2'-CO₂CH₃ | | " | 8 | 146–150 | 67.42 67.30 | 7.72 7.39 | 3.57 3.48 | — | — |
| 43 | " | 2 | —N(CH₃)₂ | | | 4'-Cl | | " | 10 | 168–169 | 63.53 63.95 | 6.81 6.90 | 4.11 3.86 | — | — |
| 44 | " | 3 | —N(CH₃)₂ | | | 4'-Cl" | | " | 10 | 153–154 | 64.41 64.55 | 7.11 7.21 | 3.95 3.73 | 0.6 | 185 |
| 45 | " | 4 | —N(CH₃)₂ | | | 4'-Cl | | 2HCl | 9 | 172–175 | 58.84 58.73 | 7.20 6.95 | 5.72 5.84 | 3.0 | — |
| 46 | " | 4 | 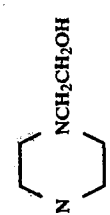 | | | 4'-Cl | | (COOH)₂ | 9 | 148–151 | 64.35 64.70 | 6.75 6.93 | 3.13 3.01 | 1.3 | — |
| 47 | " | 4 | —N(CH₃)₂ | | | 2'-Cl | | HCl | 8 | 122–123 | 65.22 65.51 | 7.39 7.09 | 3.80 3.81 | 0.5 | 170 |
| 48 | " | 2 | —N(CH₃)₂ | | | 2'-Cl | | " | 10 | 202–203 | 63.53 63.41 | 6.81 7.17 | 4.11 4.04 | — | — |
| 49 | " | 4 | 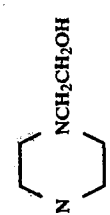 | | | 2'-Cl | | 2HCl | 9 | 181–184 | 58.84 59.01 | 7.20 7.12 | 5.72 5.84 | — | — |

TABLE 1-continued

Compound:

structure with Y1, Y1', Y2, and -O(CH2)nR group on biphenyl-CH2CH2 system

| Sample No. | Position of —O(CH2)nR group | n | R | Y1' | Y2' | Addition moiety | Preparation process (Ex. No.) | m.p. (°C.) | Elementary analysis Upper: Calcd. (%) Lower: Found (%) C | H | N | I50 (μ Mol) | ID50 (mg/kg i.p. in mice) |
|---|---|---|---|---|---|---|---|---|---|---|---|---|---|
| 50 | " | 4 | -N(piperidine) | 2'-Cl | " | HCl | 9 | 153-155 | 67.64 / 67.37 | 7.65 / 7.81 | 3.43 / 3.64 | — | — |
| 51 | " | 6 | —N(CH3)2 | 2'-Cl | " | " | 8 | 141-143 | 66.66 / 66.85 | 7.88 / 7.63 | 3.53 / 3.44 | 0.8 | 250 |
| 52 | " | 3 | —N(CH3)2 | 2'-Cl | " | " | 10 | 135-136 | 64.41 / 64.20 | 7.11 / 7.21 | 3.95 / 4.11 | 0.65 | — |
| 53 | " | 4 | 4-CH3-piperidine | 2'-Cl | " | " | 9 | 142 | 68.24 / 67.97 | 7.87 / 7.99 | 3.32 / 3.18 | — | — |
| 54 | " | 3 | —N(CH3)2 | 3'-Cl | 4'-Cl | " | 10 | 136-137 | 58.70 / 58.65 | 6.22 / 6.11 | 3.60 / 3.53 | 0.6 | 250 |
| 55 | " | 4 | —N(CH3)2 | 4'-F | H | " | 8 | 137 | 68.27 / 68.18 | 7.73 / 7.83 | 3.98 / 3.85 | 0.75 | 185 |
| 56 | " | 4 | —N(CH3)2 | 4'-F | " | — | 9 | 82-84 | 72.33 / 72.01 | 7.84 / 7.73 | 7.03 / 7.21 | 1.3 | 450 |
| 57 | " | 4 | 4-CONH2-piperidine | 4'-F | " | HCl | 4 | 165-167 | 66.12 / 66.35 | 7.17 / 7.03 | 3.21 / 3.18 | — | — |
| 58 | " | 4 | 4-CO2H-piperidine | 4'-F | " | " | 9 | 177-178 | 67.72 / 67.43 | 7.66 / 7.85 | 3.43 / 3.61 | 1.1 | — |
| | " | 4 | 4-OH-piperidine | | | | | | | | | | |

TABLE 1-continued

Compound structure: Y₁, Y₂ substituted phenyl — CH₂CH₂ — phenyl (Y₁', Y₂') with O(CH₂)ₙR group

| Sample No. | Position of —O(CH₂)ₙR group | n | R | Y₁ | Y₁' | Y₂' | Addition moiety | Preparation process (Ex. No.) | m.p. (°C.) | Elementary analysis Upper: Calcd. (%) / Lower: Found (%) C | H | N | $I_{50}$ (μ Mol) | $ID_{50}$ (mg/kg i.p. in mice) |
|---|---|---|---|---|---|---|---|---|---|---|---|---|---|---|
| 59 | " | 4 | 4-CON(CH₃)₂-piperidin-N-yl | " | 4'-F | " | " | 9 | 149–152 | 67.44 / 67.57 | 7.84 / 7.99 | 6.05 / 5.93 | — | — |
| 60 | " | 4 | 4-CO₂Et-piperidin-N-yl | " | 4'-F | " | " | 9 | 91–93 | 67.30 / 67.11 | 7.60 / 7.53 | 3.02 / 3.30 | — | — |
| 61 | " | 4 | —N(CH₃)₂ | " | 2'-CH₃ | " | " | 8 | 146–147 | 72.49 / 72.61 | 8.69 / 8.66 | 4.03 / 4.13 | 1.1 | — |
| 62 | " | 4 | piperazin-N-yl-N'-CH₃ | " | 2'-CH₃ | " | 2HCl | 9 | 195–198 | 65.59 / 65.85 | 8.26 / 8.03 | 6.37 / 6.45 | — | — |
| 63 | " | 4 | 4-CONH₂-piperidin-N-yl | " | 2'-CH₃ | " | — | 9 | 97–100 | 76.10 / 76.41 | 8.69 / 8.53 | 7.10 / 7.22 | 2.0 | — |
| 64 | " | 3 | —N(CH₃)₂ | " | 4'-N(CH₃)₂ | " | 2HCl | 10 | 164–167 | 63.15 / 63.38 | 8.08 / 7.91 | 7.01 / 7.23 | 0.35 | — |
| 65 | " | 4 | —N(CH₃)₂ | " | 4'-N(CH₃)₂ | " | " | 9 | 157–159 | 62.89 / 63.05 | 7.92 / 8.11 | 8.46 / 8.32 | — | — |
| 66 | " | 3 | —N(CH₃)₂ | 5-Cl | H | " | HCl | 10 | 122–124 | 64.41 / 64.68 | 7.11 / 6.98 | 3.95 / 3.67 | — | — |
| 67 | " | 4 | —N(CH₃)₂ | 3-OCH₃ | " | " | " | 8 | 117 | 69.31 / 69.28 | 8.31 / 8.44 | 3.85 / 3.93 | 3.0 | — |

Having now fully described the invention, it will be apparent to one of ordinary skill in the art that many changes and modifications can be made thereto without departing from the spirit of the invention as set forth herein.

What is claimed as new and intended to be covered by Letters Patent is:

1. A compound which is 2-(2-dimethylaminoethoxy)-bibenzyl.
2. A compound which is 2-(4-dimethylaminobutoxy)-bibenzyl.
3. A compound which is 2-(4-diethylaminobutoxy)bibenzyl.
4. A compound which is 2-(3-dimethylaminopropoxy)-5-chlorobibenzyl.

* * * * *